United States Patent
Lee et al.

(10) Patent No.: US 12,185,683 B2
(45) Date of Patent: Jan. 7, 2025

(54) CULTURING APPARATUS FOR CULTURING POTATO TISSUE

(71) Applicant: E GREEN GLOBAL CO., LTD., Gunpo-Si (KR)

(72) Inventors: Dong Keun Lee, Naksan-Gil (KR); Dong Won Lee, Gunpo-Si (KR)

(73) Assignee: E GREEN GLOBAL CO., LTD., Gunpo-si (KR)

(*) Notice: Subject to any disclaimer, the term of this patent is extended or adjusted under 35 U.S.C. 154(b) by 0 days.

(21) Appl. No.: 18/047,676

(22) Filed: Oct. 19, 2022

(65) Prior Publication Data

US 2023/0301258 A1    Sep. 28, 2023

(30) Foreign Application Priority Data

Mar. 22, 2022  (KR) .................. 10-2022-0035622

(51) Int. Cl.
*A01H 4/00*    (2006.01)

(52) U.S. Cl.
CPC .................... *A01H 4/001* (2013.01)

(58) Field of Classification Search
CPC .......... A01G 9/24; A01G 9/249; A01G 9/246; A01G 9/245; A01G 9/023; A01G 31/06;
(Continued)

(56) References Cited

U.S. PATENT DOCUMENTS 4,015,366 A * 4/1977 Hall, III .............. A01G 3/04
    193/25 E
5,570,540 A * 11/1996 Womack ............. A47G 7/041
    47/60

(Continued)

FOREIGN PATENT DOCUMENTS

CN    2750650 Y    1/2006
CN    205320548 U  * 6/2016
(Continued)

OTHER PUBLICATIONS

Search Report issued in Dutch Application No. 2033341, mailed on Apr. 24, 2023 (8 pages).
(Continued)

*Primary Examiner* — Tien Q Dinh
*Assistant Examiner* — Kevin M Dennis
(74) *Attorney, Agent, or Firm* — Osha Bergman Watanabe & Burton LLP

(57) ABSTRACT

The present invention relates to a culturing apparatus for culturing potato tissue, the culturing apparatus including a culture table including a plurality of vertical frame parts erected to be spaced apart from each other and a horizontal frame part connecting the vertical frame parts, a shelf part which slidably moves on the horizontal frame part, on which a culture container which accommodates a plantlet cultured in a medium is seated and which includes a plurality of hole parts on a bottom surface thereof, a light emitting diode (LED) light source unit that is installed in the culture table and irradiates the culture container with a light beam, a condensation measurement unit that is installed in the shelf part and measures condensation generated in the culture container by irradiating the culture container with infrared rays, and a cooling unit that is installed in the culture table, is electrically connected to the condensation measurement unit, and circulates cooling water passing through the LED light source unit according to condensation information measured by the condensation measurement unit, and thus controls a temperature of the LED light source unit.

5 Claims, 8 Drawing Sheets

(58) Field of Classification Search
CPC ......... A01G 7/045; F21V 29/00; F21V 29/50; F21V 29/56; F21V 29/61; A01H 4/001
USPC .......... 47/83, 82, 59 R, 62 R, 63, 17, 39, 89
See application file for complete search history.

(56) References Cited

U.S. PATENT DOCUMENTS

| | | | |
|---|---|---|---|
| 10,309,896 B2* | 6/2019 | Fujiyama | G01N 21/359 |
| 10,768,102 B2* | 9/2020 | Fujiyama | A01G 25/165 |
| 11,660,830 B2* | 5/2023 | Rotter | B29C 70/462 |
| | | | 244/129.1 |
| 2013/0021797 A1* | 1/2013 | Kubo | A01G 9/249 |
| | | | 362/235 |
| 2018/0284016 A1* | 10/2018 | Fujiyama | A01G 7/04 |
| 2019/0029187 A1* | 1/2019 | Brault | H05B 45/14 |
| 2019/0310206 A1* | 10/2019 | Na | G01N 21/53 |
| 2019/0364743 A1* | 12/2019 | Lys | A01G 7/045 |
| 2020/0231267 A1* | 7/2020 | Rotter | B64F 5/10 |
| 2021/0144942 A1* | 5/2021 | Ofir | A01G 7/045 |
| 2021/0360873 A1* | 11/2021 | Ofray | A01G 9/246 |

FOREIGN PATENT DOCUMENTS

| | | | | |
|---|---|---|---|---|
| CN | 106171973 | A | | 12/2016 |
| CN | 107683086 | A | | 2/2018 |
| CN | 107873165 | A | | 4/2018 |
| CN | 107996383 | A | | 5/2018 |
| CN | 207560931 | U | | 7/2018 |
| CN | 111134017 | A | | 5/2020 |
| CN | 212013989 | U | | 11/2020 |
| CN | 212544988 | U | | 2/2021 |
| CN | 115682608 | A | * | 2/2023 |
| EP | 2556745 | A1 | | 2/2013 |
| JP | 2010-085346 | A | | 4/2010 |
| JP | 2012024042 | A | | 2/2012 |
| JP | 5261612 | B2 | | 8/2013 |
| KR | 20120128375 | A | | 11/2012 |
| KR | 20150135857 | A | | 12/2015 |
| KR | 20160126249 | A | * | 11/2016 |
| KR | 101693419 | B1 | | 1/2017 |
| WO | 0203777 | A1 | | 1/2002 |
| WO | 2011125382 | A1 | | 10/2011 |
| WO | 2014157671 | A1 | | 10/2014 |
| WO | WO-2019040944 | A9 | * | 5/2019 ............. A01G 31/06 |
| WO | 20200231267 | A1 | | 11/2020 |
| WO | 2022025674 | A1 | | 2/2022 |

OTHER PUBLICATIONS

Zabel et al.; "Future Exploration Greenhouse Design of the EDEN ISS Project;" 47th International Conference on Environmental Systems; Jul. 16-20, 2016; pp. 1-13 (13 pages).

Maiwald et al.; "From Ice to Space: A Greenhouse Design for Moon or Mars Based on a Prototype Deployed in Antarctica;" CEAS Space Journal; 2021; pp. 17-37 (21 pages).

"Executive Summary: EDEN ISS, Ground Demonstration of Plant Cultivation Technologies for Safe Food Production in Space;" Jun. 24, 2019; Retrieved from the Internet: URL: https://eden-iss.net/wp-content/uploads/EDEN-ISS-Complete-Brochure_ONLINE_small.pdf (47 pages).

Examination Report issued in Saudi Arabian Application No. 122440625 mailed on Sep. 29, 2023 (6 pages).

Office Action issued in Korean Application No. 10-2022-0035622 mailed on May 30, 2024 (9 pages).

Wang, J. et al. "Design of Space Plant Cultivation Device and Environmental Monitoring System" Nov. 25, 2013 Lanzhou Physics Institute (5 pages).

Office Action issued in corresponding CN Application No. 202211501445.9 dated Jun. 6, 2024 (9 pages).

* cited by examiner

CULTURING APPARATUS FOR CULTURING POTATO TISSUE

CROSS-REFERENCE TO RELATED APPLICATION

This application claims the benefit under 35 U.S.C. § 119(a) of priority to Korean Patent Application No. 10-2022-0035622 filed on Mar. 22, 2022 in the Korean Intellectual Property Office, the entire disclosure of which is incorporated herein by reference for all purposes.

BACKGROUND

Technical Field

Exemplary embodiments of the present disclosure relate to a culturing apparatus for culturing potato tissue, and more particularly, to a culturing apparatus for culturing potato tissue that can prevent condensation generated in a culture container when potato tissue is cultured.

Discussion of the Background

In general, plant tissue culture refers to the growth of plant tissues, organs, cells, or the like by providing necessary nutrients, plant hormones, or the like to a culture container.

This plant tissue culture technology is being used as an effective technology in various fields such as mass propagation of individuals, molecular breeding, and production of plant materials through mass culture.

Meanwhile, in the plant tissue culture, the culture container which accommodates a plantlet cultured in a medium is provided in a culture table, and the plant tissue is cultured using an artificial light source for photosynthesis, which is installed in the culture table.

The artificial light source, from which light is irradiated so that a photosynthetic action is generated in the plantlet while the plant tissue is cultured, emits heat by itself, and thus the inside of the culture table is maintained above a predetermined temperature.

In particular, when the artificial light source is overheated, moisture in the medium accommodated in the culture container is evaporated due to a rapid temperature rise in the culture table, and condensation in which water drops are formed on an inner surface of the culture container occurs due to the evaporation of the moisture.

When condensation occurs inside the culture container, light transmission efficiency is lowered, and thus the plant tissue cannot be grown properly. Further, the water drops condensed on the inner surface of the culture container drop onto the plant tissue, and thus the plant tissue is secondarily contaminated.

In order to solve these problems, in the related art, a blower device is installed in the culture table to control the temperature inside the culture table through an air circulation method.

However, in the temperature control method through air circulation according to the related art, the inside of the culture table is contaminated due to wind.

The background technology of the present invention is disclosed in Korean Patent Publication No. 10-1693419 (registered on Jan. 5, 2017, title of the invention: Table for Plant Tissue Culture).

SUMMARY

The present invention is directed to providing a culturing apparatus for culturing potato tissue that can prevent condensation generated in a culture container when potato tissue is cultured by cooling heat generated from an artificial light source for photosynthesis and controlling a temperature of a culture table.

One aspect of the present invention provides a culturing apparatus for culturing potato tissue, the culturing apparatus including a culture table including a plurality of vertical frame parts erected to be spaced apart from each other and a horizontal frame part connecting the vertical frame parts, a shelf part which slidably moves on the horizontal frame part, on which a culture container accommodating a plantlet cultured in a medium is seated and which includes a plurality of hole parts on a bottom surface thereof, a light emitting diode (LED) light source unit that is installed in the culture table and irradiates the culture container with a light beam, a condensation measurement unit that is installed in the shelf part and measures condensation generated in the culture container by irradiating the culture container with infrared rays, and a cooling unit that is installed in the culture table, is electrically connected to the condensation measurement unit, and circulates cooling water passing through the LED light source unit according to condensation information measured by the condensation measurement unit, and thus controls a temperature of the LED light source unit.

The culture table may further include an upper plate part coupled to upper end portions of each of respective vertical frame parts.

The horizontal frame part may include an upper frame portion spaced apart from and provided below the upper plate part, and a lower frame portion spaced apart from and provided below the upper frame portion.

The shelf part may include a first shelf portion slidably coupled to the upper frame portion, and a second shelf portion slidably coupled to the lower frame portion.

The LED light source unit may include a first light source unit installed on a bottom surface of the upper plate part, and a second light source unit installed below the first shelf portion.

The condensation measurement unit may include a light emission unit that is installed a first surface inside the shelf part and irradiates an outer surface of the culture container with infrared rays, a light reception unit that is installed on a second surface inside the shelf part and detects infrared rays irradiated from the light emission unit and passing through the culture container, and a light quantity measurement module that measures a light quantity of the infrared rays detected by the light reception unit.

The cooling unit may include a circulation pump that includes an inlet port through which the cooling water is suctioned and an outlet port through which the cooling water is discharged and pumps the cooling water so that the cooling water circulates from the outlet port to the inlet port, a heat dissipation unit that is mounted on a side of the inlet port of the circulation pump and dissipates heat of the cooling water suctioned to the circulation pump, and a cooling water transfer line that is provided through the LED light source unit and is connected to the outlet port of the circulation pump and the heat dissipation unit to transfer the cooling water.

The culturing apparatus may further include a culture container fixing unit that fixes the culture container to the shelf part using an attractive force between the culture container and the shelf part.

The culture container fixing unit may include an iron plate provided on a bottom surface of an outer side of the culture container, and an electromagnet provided on a bottom surface of an outer side of the shelf part.

The culture container fixing unit may further include a switch unit that performs on-off controls of a current applied to the electromagnet.

The switch unit may include a nonconductor provided at a rear end of the outer side of the electromagnet; and an electrical connecting rod in contact with an outer surface of the electromagnet to transfer the current to the electromagnet, and when the shelf part is moved and exposed toward a front side of the culture table, the electrical connecting rod comes into contact with an outer surface of the nonconductor, and thus the current applied to the electromagnet is cut off.

The shelf part may be made of a non-metallic material.

The culturing apparatus for culturing potato tissue according to the present invention, through a condensation measurement unit that measures condensation generated on an inner surface of a culture container by irradiating the culture container with infrared rays in a non-contact manner, heat generated by a light emitting diode (LED) light source unit is cooled, a temperature of the culture table is maintained at a constant level, and thus the condensation generated in the culture container while potato tissue is cultured can be prevented. This helps the growth of a plantlet, thereby improving productivity.

Further, according to the present invention, through a culture container fixing unit for fixing the culture container to the shelf part using an attractive force through a magnetic force between the culture container and the shelf part, the culture container can be firmly fixed to prevent the culture container from being easily separated from the shelf part even when an earthquake occurs or an external force is applied to the culture table.

DETAILED DESCRIPTION OF THE ILLUSTRATED EMBODIMENTS

Figure 1:
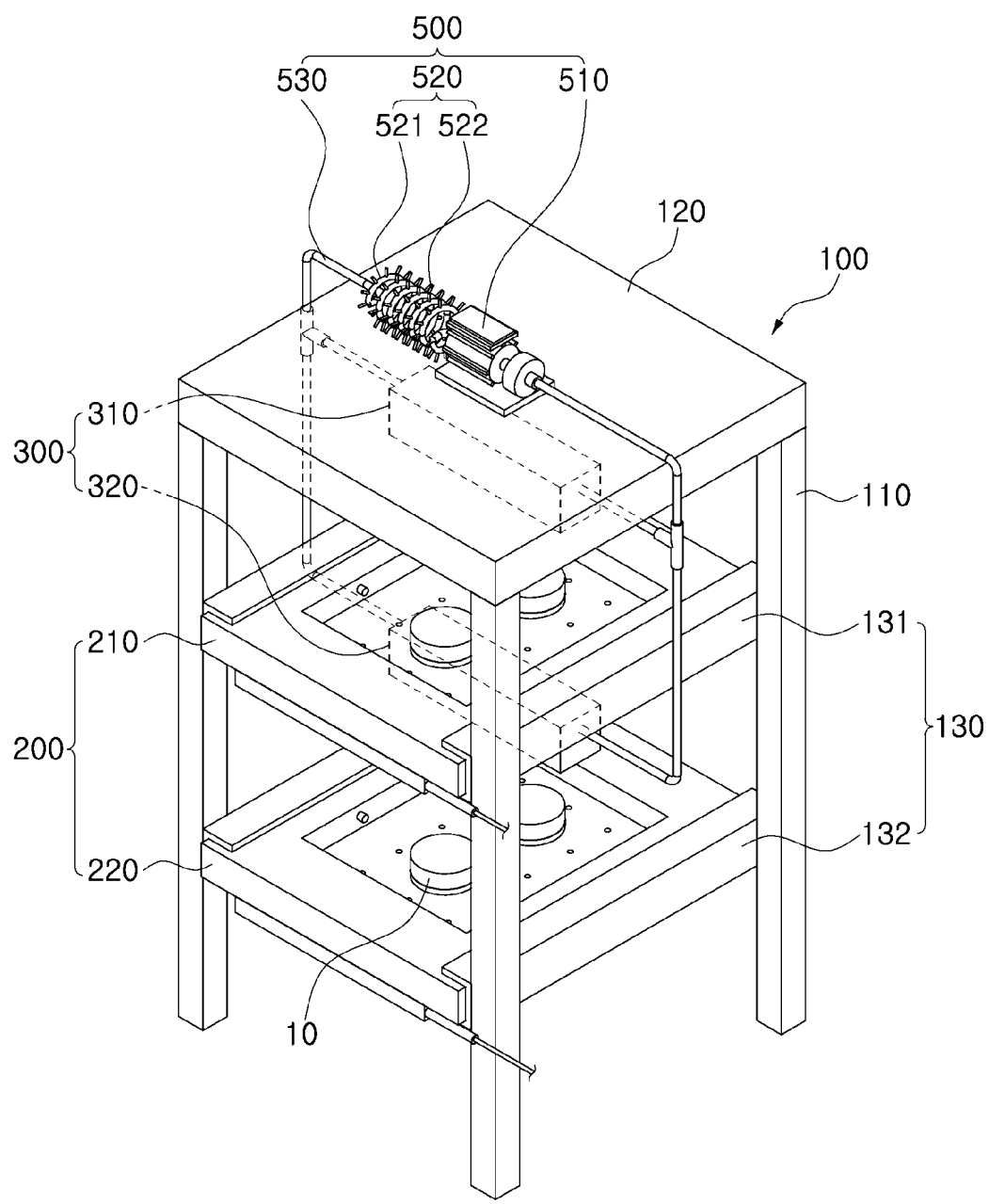
FIGS. 1 and 2 are perspective views illustrating a culturing apparatus for culturing potato tissue according to an embodiment of the present invention.

Hereinafter, a culturing apparatus for culturing potato tissue according to an embodiment of the present invention will be described with reference to the accompanying drawings. In this process, the thicknesses of lines or the sizes of components illustrated in the drawings may be exaggerated for clarity and convenience of description.

Furthermore, terms described below are terms defined in consideration of functions in the present invention and may change according to the intention or custom of a user or an operator. Therefore, definitions of these terms should be made based on the contents throughout the present specification.

Figure 2:
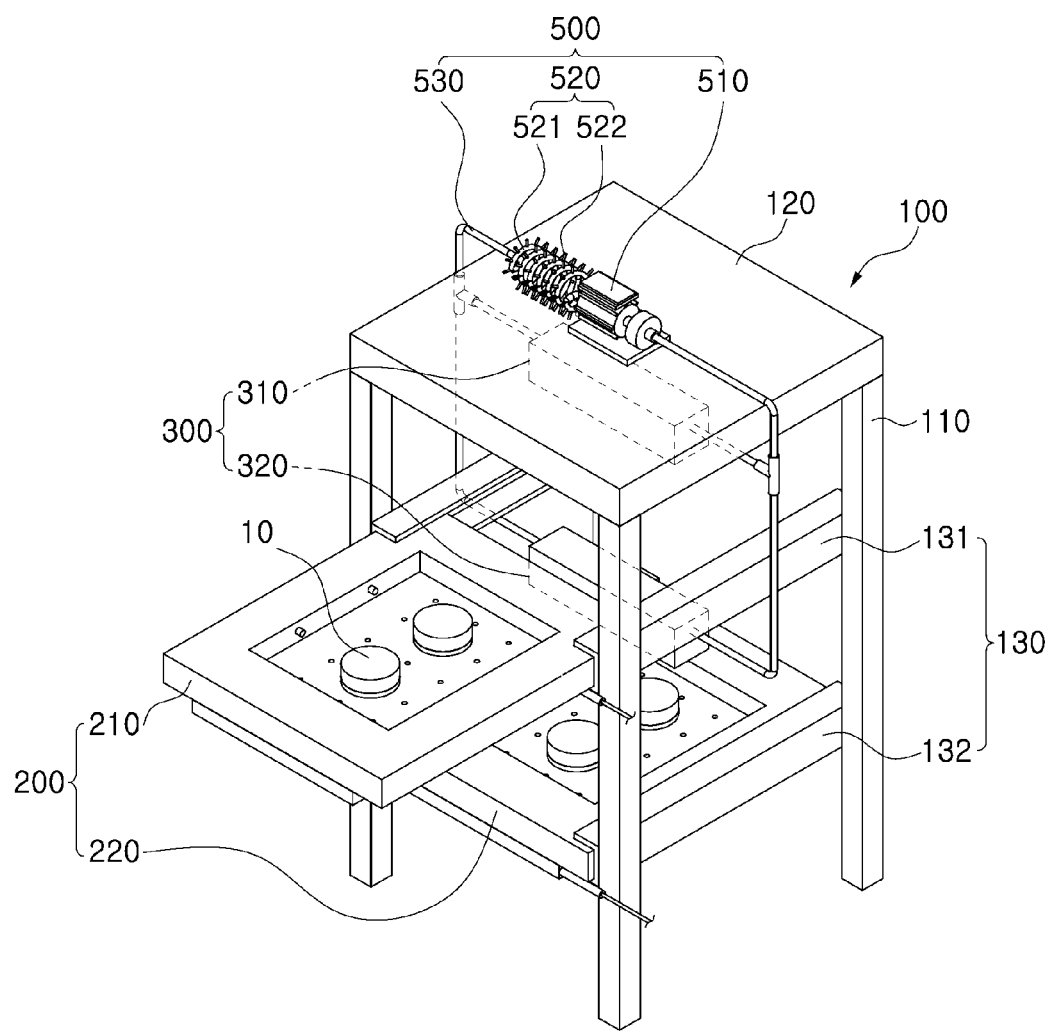
Figure 3:
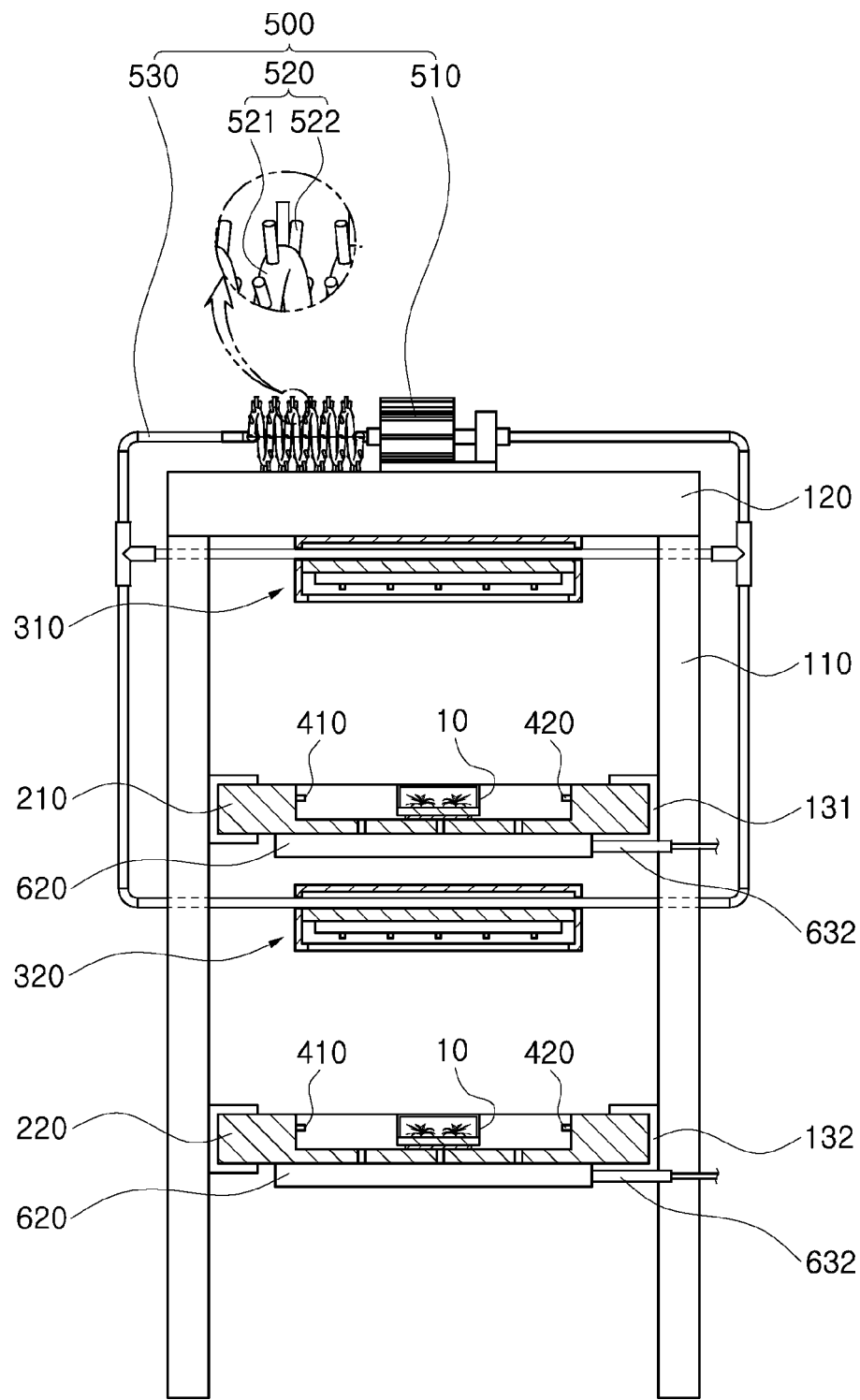
FIG. 3 is a front cross-sectional view illustrating the culturing apparatus for culturing potato tissue according to an embodiment of the present invention.
Figure 4:
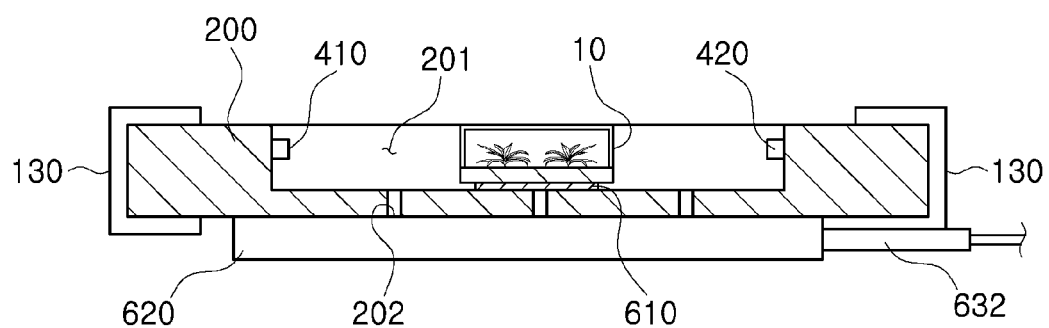
FIG. 4 is a partial cross-sectional view illustrating the culturing apparatus for culturing potato tissue according to an embodiment of the present invention.
Figure 5:
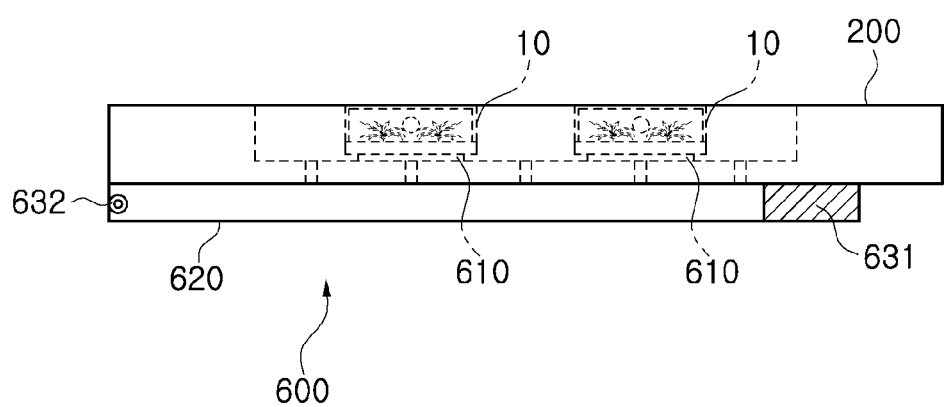
FIG. 5 is a side cross-sectional view illustrating a shelf part accommodated inside a culture table in the culturing apparatus for culturing potato tissue according to an embodiment of the present invention.
Figure 6:
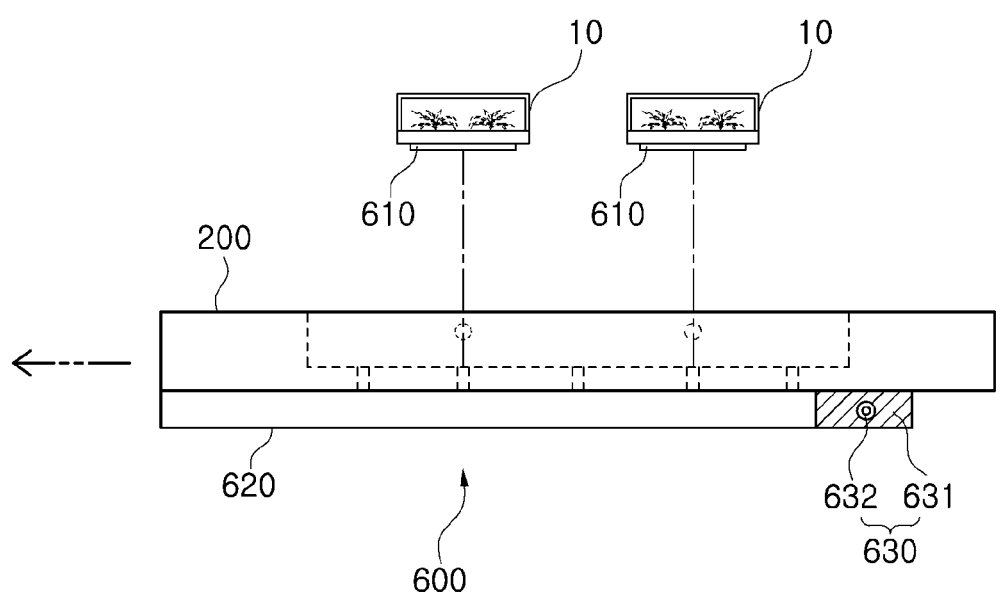
FIG. 6 is a side cross-sectional view illustrating the shelf part moved to the front side of the culture table in the culturing apparatus for culturing potato tissue according to an embodiment of the present invention.
Figure 7:
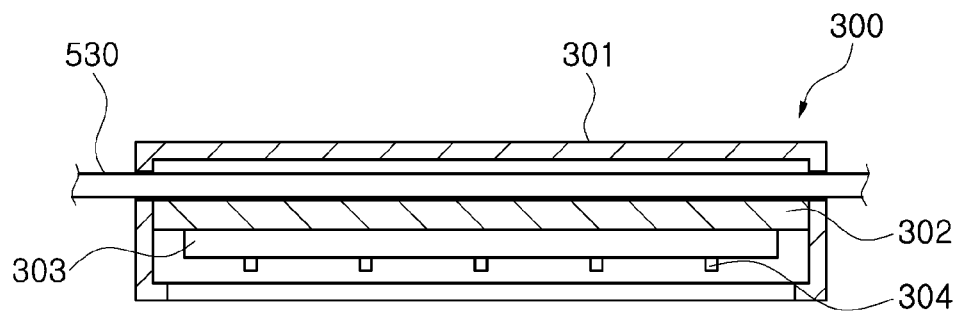
FIG. 7 is a front cross-sectional view illustrating a light emitting diode (LED) light source unit in the culturing apparatus for culturing potato tissue according to an embodiment of the present invention.
Figure 8:
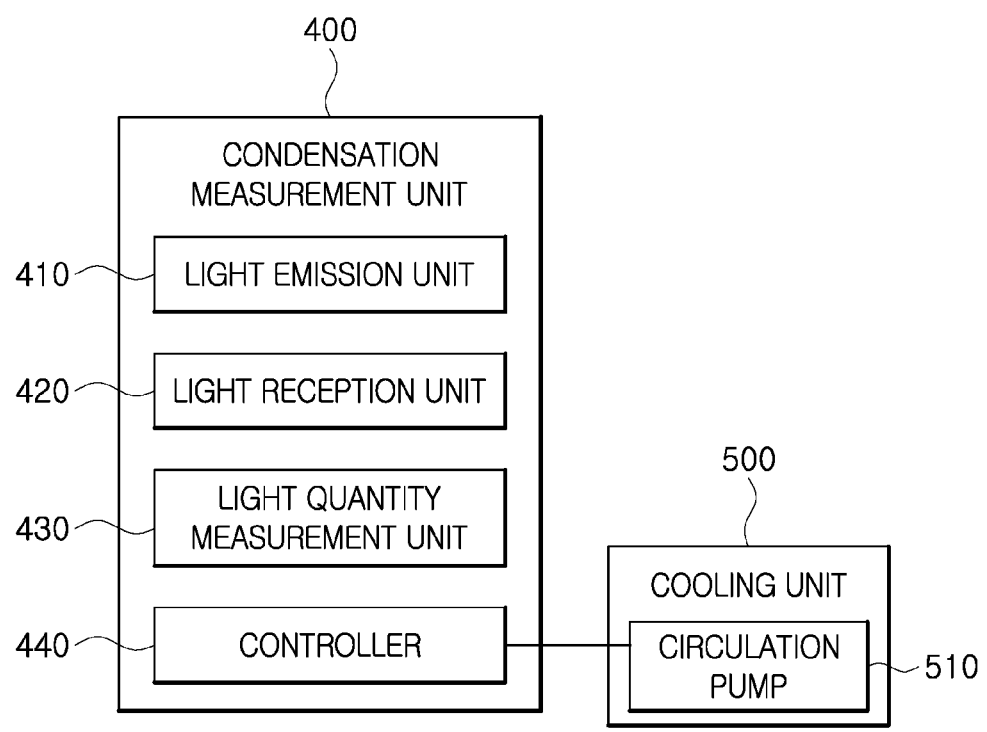
FIG. 8 is a diagram illustrating a connection relationship between a condensation measurement unit and a cooling unit in the culturing apparatus for culturing potato tissue according to an embodiment of the present invention.

FIGS. 1 and 2 are perspective views illustrating a culturing apparatus for culturing potato tissue according to an embodiment of the present invention, FIG. 3 is a front cross-sectional view illustrating the culturing apparatus for culturing potato tissue according to an embodiment of the present invention, FIG. 4 is a partial cross-sectional view illustrating the culturing apparatus for culturing potato tissue according to an embodiment of the present invention, FIG. 5 is a side cross-sectional view illustrating a shelf part accommodated inside a culture table in the culturing apparatus for culturing potato tissue according to an embodiment of the present invention, FIG. 6 is a side cross-sectional view illustrating the shelf part moved to the front side of the culture table in the culturing apparatus for culturing potato tissue according to an embodiment of the present invention, FIG. 7 is a front cross-sectional view illustrating an light emitting diode (LED) light source unit in the culturing apparatus for culturing potato tissue according to an embodiment of the present invention, and FIG. 8 is a diagram illustrating a connection relationship between a condensation measurement unit and a cooling unit in the culturing apparatus for culturing potato tissue according to an embodiment of the present invention.

Referring to FIGS. 1 to 8, the culturing apparatus for culturing potato tissue according to an exemplary embodiment of the present invention includes a culture table 100, a shelf part 200, an LED light source unit 300, a condensation measurement unit 400, a cooling unit 500, and a culture container fixing unit 600.

The culture table 100 has a prismatic structure having a rectangular bottom surface and open front, rear, left, and right sides, and includes a vertical frame part 110, an upper plate part 120, and a horizontal frame part 130.

The vertical frame part 110 is a rod-shaped member having a predetermined length, and a plurality of vertical frame parts 110 are arranged to be spaced apart from each other and vertically erected at positions of corners of the culture table 100.

The upper plate part 120 is a flat plate-shaped member, is formed to shield an open support portion of the culture table 100, is horizontally seated on the vertically erected vertical frame part 110, and is horizontally coupled to upper ends of each of the vertical frame parts 110.

The horizontal frame part 130 is orthogonal to the vertical frame parts 110 and horizontally connects the vertical frame parts 110 in a front-rear direction on both left and right sides of the culture table 100. The horizontal frame part 130 has a shape in which both ends are opened and an opening is formed in an outer surface thereof and which has a "C"-shaped cross-section.

The horizontal frame part 130 is provided inside the culture table 100 in a state in which the openings formed in the outer surface thereof face each other and is coupled to an outer surface of the vertical frame part 110.

The horizontal frame part 130 may include an upper frame portion 131 and a lower frame portion 132. The upper frame portion 131 is spaced apart from the upper plate part 120, provided below the upper plate part 120, and is coupled to upper sides of each of the vertical frame parts 110.

The lower frame portion 132 is spaced apart from the upper frame portion 131, is provided below the upper frame portion 131, and is coupled to a lower side of each of the vertical frame parts 110. Thus, the upper frame portion 131 and the lower frame portion 132 are arranged to be vertically spaced apart from each other.

The shelf part 200 is a flat plate-shaped member, and a culture container 10 which accommodates a plantlet cultured in a medium and which is made of a transparent material is accommodated in the shelf part 200.

The plantlet accommodated in the culture container 10 is a potato tissue cultured plantlet as an embodiment, but the present invention is not limited thereto, and the plantlet may be changed to various types of plant tissue plantlets.

The shelf part 200 is made of a non-metallic material that does not conduct electricity, such as plastic, wood, and glass.

A downwardly concave engraved seating part 201 is formed on an upper surface of the shelf part 200 except for an edge of the shelf part 200. The shelf part 200 may include a plurality of holes 202 vertically formed so that air may flow onto a bottom surface of the seating part 201 on which the culture container 10 is seated.

The shelf part 200 is horizontally rail-coupled to an inside of the horizontal frame part 130.

Both left and right ends of the shelf part 200 are inserted into the horizontal frame part 130 through open front ends of the horizontal frame part 130 arranged on both sides of the shelf part 200, and the shelf part 200 linearly and slidably moves in a lengthwise direction (axial direction) of the horizontal frame part 130. That is, the shelf part 200 is slidably installed on the horizontal frame part 130.

Thus, the shelf part 200 may be extracted from or retracted into a front side of the culture table 100 through a front surface of the culture table 100.

The shelf part 200 may include a first shelf portion 210 and a second shelf portion 220. The first shelf portion 210 is rail-coupled to the upper frame portion 131, and the second shelf portion 220 is rail-coupled to the lower frame portion 132.

That is, the first shelf portion 210 is slidably installed on the upper frame portion 131, and the second shelf portion 220 is slidably installed on the lower frame portion 132.

Thus, the first shelf portion 210 and the second shelf portion 220 of the shelf part 200 are configured in multiple stages to be vertically spaced apart from each other.

The LED light source unit 300 is provided in the culture table 100 and serves to irradiate the culture container 10 seated on the shelf part 200 with an LED light beam to perform a photosynthetic reaction of the plantlet accommodated in the culture container 10.

The LED light source unit 300 has a hollow shape, is made of a transparent material so that light is transmitted therethrough, and includes a housing 301 having a partition wall 302 in a lengthwise direction such that an inner space is partitioned vertically.

A lower space inside the housing 301 partitioned by the partition wall 302 includes a printed circuit board (PCB) 303 installed on a lower surface of an outer side of the partition wall 302 and an LED element 304 surface-mounted on a lower surface of an outer side of the PCB 303.

In an upper space inside the housing 301, a cooling water transfer line 530 of the cooling unit 500, which will be described below, is inserted into the housing 301 in a lengthwise direction.

The LED light source unit 300 includes a first light source unit 310 and a second light source unit 320.

The first light source unit 310 is fixedly installed on a bottom surface of an outer side of the upper plate part 120 and irradiates the culture container 10 seated on an upper surface of the first shelf portion 210 with an LED light beam.

The second light source unit 320 is provided below the first shelf portion 210, and irradiates the culture container 10 seated on an upper surface of the second shelf portion 220 with an LED light beam.

The second light source unit 320 is not fixedly installed in the first shelf portion 210 and is installed to be spaced apart from the first shelf portion 210 so as not to interfere with a sliding linear movement of the first shelf portion 210 rail-coupled to the upper frame portion 131.

In other words, the housing 301 is held on the cooling water transfer line 530 passing through the housing 301 of the second light source unit 320 in a lengthwise direction and passing through the upper space of the housing 301.

The condensation measurement unit 400 is installed in the first shelf portion 210 and the second shelf portion 220 to measure condensation generated on an inner surface of the culture container 10.

The condensation measurement unit 400 measures the condensation by irradiating the culture container 10 from the outside of the culture container 10 with infrared rays in a non-contact manner.

The condensation measurement unit 400 may include a light emission unit 410, a light reception unit 420, a light quantity measurement module 430, and a controller 440.

The light emission unit 410 is an optical element from which the infrared rays are emitted and is installed on a first surface of an inside of the seating part 201 formed on the upper surface of the shelf part 200. The light emission unit 410 irradiates an outer surface of the culture container 10 with the infrared rays. That is, the infrared rays are irradiated in a lateral direction of the culture container 10.

The light reception unit 420 is a sensor for detecting the infrared rays, and is installed on a second surface of the inner side of the seating part 201 formed on the upper surface of the shelf part 200 facing the light emission unit 410. The light reception unit 420 detects the infrared rays that are irradiated from the light emission unit 410 and pass through the culture container 10.

The light quantity measurement module 430 is electrically connected to the light emission unit 410 and the light reception unit 420 and measures a light quantity of the infrared rays detected by the light reception unit 420.

When the light quantity of the infrared rays irradiated from the light emission unit 410 and measured by the light quantity measurement module 430 and the light quantity of the infrared rays received by the light reception unit 420 are the same, a determination module of the controller 440 determines that the condensation is not generated in the culture container 10, and the controller 440 turns off the cooling unit 500.

When the condensation in which water drops are formed is generated on the inner surface of the culture container 10, a light quantity smaller than the total light quantity of the infrared rays irradiated from the light emission unit 410, which are scattered by the water drops or absorbed to the water drops, is received by the light reception unit 420, and the cooling unit 500 electrically connected to the condensation measurement unit 400 is operated under control of the controller 440.

In other words, a circulation pump 510 of the cooling unit 500 is operated by the controller 440, and thus cooling water circulates in the cooling water transfer line 530.

The cooling unit 500 is installed in the culture table 100 and is electrically connected to the condensation measurement unit 400. When the condensation of the culture container 10 is measured by the condensation measurement unit 400, the cooling water passing through the inside of the LED light source unit 300 circulates to control a temperature of the LED light source unit 300.

That is, the condensation measurement unit 400 measures condensation information of the culture container 10 and transmits the measured condensation information to the controller 440, and the controller 440 controls operation of the cooling unit 500 according to the received condensation information. As the cooling water circulates by the operation of the cooling unit 500, heat generated by the LED light source unit 300 can be cooled.

The cooling unit 500 may include a circulation pump 510, a heat dissipation unit 520, and the cooling water transfer line 530.

The circulation pump 510 is installed on the upper plate part 120. An inlet port through which the cooling water is suctioned and an outlet port through which the cooling water is discharged are formed on each side of the circulation pump 510.

The circulation pump 510 pumps the cooling water so that the cooling water, discharged from the outlet port, passes through the cooling water transfer line 530, which will be described below, is suctioned to the inlet port, and thus circulates.

The heat dissipation unit 520 is mounted on a side of the inlet port of the circulation pump 510. The circulation pump 510 and the heat dissipation unit 520 communicate with each other so that the cooling water flows.

The heat dissipation unit 520 serves to reduce the temperature of the cooling water by radiating heat of the cooling water suctioned to the circulation pump 510.

The heat dissipation unit 520 may include a hollow body 521 forming a coil-shaped flow path to maximally buffer the cooling water suctioned into the circulation pump 510 and a plurality of heat dissipation pins 522 formed on an outer surface of the body 521 to maximize cooling efficiency.

The cooling water transfer line 530 pass through the LED light source unit 300 and both ends thereof are connected to the outlet port of the circulation pump 510 and the heat dissipation unit 520. The cooling water is transferred through the cooling water transfer line 530.

The cooling water transfer line 530 may be made of an aluminum material having excellent thermal conductivity.

Heat generated by the PCB 303 of the LED light source unit 300 installed in the lower space inside the housing 301 can be cooled using the cooling water passing through the housing 301 of the LED light source unit 300 in a lengthwise direction and circulating through the cooling water transfer line 530 inserted into the upper space inside the housing 301.

The culture container fixing unit 600 fixes the culture container 10 to the shelf part 200 using an attractive force between the culture container 10 and the shelf part 200.

The culture container fixing unit 600 may include an iron plate 610, an electromagnet 620, and a switch unit 630.

The iron plate 610 is thin and is detachably attached to a bottom surface of an outer side of the culture container 10.

The electromagnet 620 has a flat plate shape and is mounted on a bottom surface of an outer side of the shelf part 200 to be spaced apart from and face the iron plate 610.

The switch unit 630 is an ON/OFF switch and performs on-off controls of a current applied to the electromagnet 620. the switch unit 630 includes a nonconductor 631 and an electrical connecting rod 632.

The nonconductor 631 is provided at a rear end of the outer side of the electromagnet 620. In other words, the nonconductor 631 may be made of a material, which does not conduct electricity, such as plastic, wood, and glass. The nonconductor 631 is mounted on the outer surface of the rear end of the electromagnet 620.

The electrical connecting rod 632 is provided in the culture table 100. The electrical connecting rod 632 is positioned at a front end of the culture table 100 and is installed in the vertical frame part 110.

The electrical connecting rod 632 is in contact with the outer surface of the electromagnet 620 and transfers the current to the electromagnet 620. Power is applied to the electrical connecting rod 632 from the outside.

The electrical connecting rod 632 is positioned on a side portion of the electromagnet 620, and a free end of the electrical connecting rod 632 is in contact with the outer surface of the electromagnet 620.

That is, in a state in which the shelf part 200 is positioned inside the culture table 100, the free end of the electrical connecting rod 632 is in contact with the electromagnet 620, the current is transferred to the electromagnet 620 by the electrical connecting rod 632, and the electromagnet 620 is magnetized to have a polarity.

In this case, the culture container 10 is firmly fixed to the shelf part 200 by an attractive force between the electromagnet 620 and the iron plate 610 mounted on a lower portion of the culture container 10 seated on the upper surface of the shelf part 200.

In this case, when the shelf part 200 is moved toward the front side of the culture table 100 by a user and the shelf part 200 is exposed to the front side of the culture table 100, as the electrical connecting rod 632 comes into contact with the outer surface of the nonconductor 631 positioned at a rear end of the electromagnet 620, the current applied to the electromagnet 620 is cut off.

In this way, when the current applied to the electromagnet 620 is cut off, the attractive force between the iron plate 610 and the electromagnet 620 is released, and thus a user may freely move or replace the culture container 10 fixed to the shelf part 200.

In the culturing apparatus for culturing potato tissue according to an embodiment of the present invention, through the condensation measurement unit 400 for measuring the condensation generated on the inner surface of the culture container 10 by irradiating the culture container 10 with infrared rays in a non-contact manner, the heat generated by the LED light source unit 300 is cooled, the temperature of the culture table 100 is maintained at a constant level, and thus the condensation generated in the culture container 10 while potato tissue is cultured can be prevented.

In the culturing apparatus for culturing potato tissue according to an embodiment of the present invention, through the culture container fixing unit 600 for fixing the culture container 10 to the shelf part 200 using the attractive force through a magnetic force between the culture container 10 and the shelf part 200, the culture container 10 can be firmly fixed to prevent the culture container 10 from being easily separated from the shelf part 200 even when an earthquake occurs or an external force is applied to the culture table 100.

Although the present invention has been described with reference to the embodiments illustrated in the drawings, the description is merely illustrative, and those skilled in the art to which the technology belongs can understand that various modifications and other equivalent embodiments may be made. Thus, the true technical scope of the present invention should be determined by the appended claims.

What is claimed is:

1. A culturing apparatus for culturing potato tissue, comprising:
    a culture table including a plurality of vertical frame parts erected to be spaced apart from each other and a horizontal frame part connecting the vertical frame parts;
    a shelf part which slidably moves on the horizontal frame part, on which a culture container which accommodates a plantlet cultured in a medium is seated, and which includes a plurality of hole parts on a bottom surface thereof;
    a light emitting diode (LED) light source unit that is installed in the culture table and irradiates the culture container with a light beam;
    a condensation measurement unit that is installed in the shelf part and measures condensation generated in the culture container by irradiating the culture container with infrared rays; and
    a cooling unit that is installed in the culture table, is electrically connected to the condensation measurement unit, and circulates cooling water passing through the LED light source unit according to condensation information measured by the condensation measurement unit, and thus controls a temperature of the LED light source unit,
    wherein:
    the culture table further includes an upper plate part coupled to each of the vertical frame parts,
    the condensation measurement unit includes:
    a light emission unit that is installed on a first surface inside the shelf part and irradiates an outer surface of the culture container with infrared rays;
    a light reception unit that is installed on a second surface inside the shelf part and detects infrared rays irradiated from the light emission unit and passing through the culture container; and
    a light quantity measurement module that measures a light quantity of the infrared rays detected by the light reception unit,
    the cooling unit includes:
    a circulation pump that includes an inlet port through which the cooling water is suctioned and an outlet port through which the cooling water is discharged and pumps the cooling water so that the cooling water circulates from the outlet port to the inlet port;
    a heat dissipation unit that is mounted on a side of the inlet port of the circulation pump and dissipates heat of the cooling water suctioned to the circulation pump; and
    a cooling water transfer line that is provided through the LED light source unit and is connected to the outlet port of the circulation pump and the heat dissipation unit to transfer the cooling water,
    the LED light source unit includes:
    a housing having a hollow shape, made of a transparent material so that light is transmitted therethrough, and having a partition wall such that an inner space is partitioned vertically;
    a printed circuit board installed on a lower surface inside the housing partitioned by the partition wall; and
    an LED element mounted on a lower surface of the printed circuit board,
    in an upper space inside the housing partitioned by the partition wall, the cooling water transfer line inserted into the housing in a lengthwise direction,
    the culturing apparatus further comprises:
    a culture container fixing unit that fixes the culture container to the shelf part using an attractive force between the culture container and the shelf part,
    the culture container fixing unit includes:
    an iron plate detachably attached to the culture container;
    an electromagnet provided on the shelf part; and
    a switch unit that performs on-off controls of a current applied to the electromagnet,
    the switch unit includes:
    a nonconductor attached to the electromagnet; and
    an electrical connecting rod to transfer the current to the electromagnet, and
    when the shelf part is disposed underneath the upper plate part, a current is applied to the electromagnet as the electromagnet contacts the electrical connecting rod,
    when the shelf part is moved on the culture table so that the shelf part is exposed outwardly of the upper plate part, the electrical connecting rod comes into contact with the nonconductor, and thus the current applied to the electromagnet is cut off.

2. The culturing apparatus of claim 1, wherein the horizontal frame part includes:
    an upper frame portion spaced apart from the upper plate part and provided below the upper plate part; and
    a lower frame portion spaced apart from the upper frame portion and provided below the upper frame portion.

3. The culturing apparatus of claim 2, wherein the shelf part includes:
    a first shelf portion slidably coupled to the upper frame portion; and
    a second shelf portion slidably coupled to the lower frame portion.

4. The culturing apparatus of claim 3, wherein the LED light source unit includes:
    a first light source unit installed on a bottom surface of the upper plate part; and
    a second light source unit installed below the first shelf portion.

5. The culturing apparatus of claim 1, wherein the shelf part is made of a non-metallic material.

* * * * *